US006345195B1

(12) United States Patent
Herskowits et al.

(10) Patent No.: US 6,345,195 B1
(45) Date of Patent: Feb. 5, 2002

(54) METHODS AND APPARATUS FOR 3D SCANNING OF THE HUMAN BODY FORM

(76) Inventors: Varda Herskowits, 16 Shapira Street, Petach-Tikva 49491; Menachem Tipris, 38C Haschafim Street, Ra'anana 43724, both of (IL)

( * ) Notice: Subject to any disclaimer, the term of this patent is extended or adjusted under 35 U.S.C. 154(b) by 0 days.

(21) Appl. No.: 09/435,834

(22) Filed: Nov. 8, 1999

(30) Foreign Application Priority Data

Sep. 29, 1999 (IL) .................................................. 132138

(51) Int. Cl.[7] .................................................. A61B 5/00
(52) U.S. Cl. .................................... 600/473; 600/476
(58) Field of Search ................................ 600/407, 310, 600/473, 476; 382/128

(56) References Cited

U.S. PATENT DOCUMENTS

| | | | |
|---|---|---|---|
| 5,069,214 A | * 12/1991 | Samaras et al. | 128/633 |
| 5,526,812 A | * 6/1996 | Dumoulin et al. | 128/653.1 |
| 5,741,215 A | * 4/1998 | D'Urso | 600/407 |
| 5,772,593 A | * 6/1998 | Hakamata | 600/407 |
| 5,836,872 A | * 11/1998 | Kenet et al. | 600/306 |
| 5,930,769 A | 7/1999 | Rose | |
| 6,032,070 A | * 2/2000 | Flock et al. | 600/473 |
| 6,178,340 B1 | * 1/2001 | Svetliza | 600/310 |

* cited by examiner

Primary Examiner—Marvin M. Lateef
Assistant Examiner—Eleni Mantis Mercader
(74) Attorney, Agent, or Firm—Eitan, Pearl, Latzer & Cohen-Zedek (57) ABSTRACT

A method for scanning an inner surface through an outer layer of material, the method including the steps of a) creating an energy beam with a wavelength, intensity, cross-section, and impact angle that, when impacted onto the outer layer of material, is sufficient to be at least partly reflected by the outer layer of material, thereby forming an outer-layer reflected beam to be at least partly transmitted in a first direction through the outer layer of material and onto the inner surface, to be at least partly reflected by the inner surface, thereby forming an inner-surface reflected beam, and to be at least partly transmitted in a second direction through the outer layer of material, b) impacting the energy beam onto the outer layer of material, c) detecting the outer-layer reflected beam and inner-surface reflected beam, d) distinguishing between the outer-layer reflected beam and inner-surface reflected beam, and e) determining from the inner-surface reflected beam a point of incidence between the energy beam and the inner surface in three dimensions.

12 Claims, 7 Drawing Sheets

METHODS AND APPARATUS FOR 3D SCANNING OF THE HUMAN BODY FORM

FIELD OF THE INVENTION

The present invention relates to three-dimensional (3D) scanning devices in general, and more particularly to improved methods and apparatus for 3D scanning of the human body form.

BACKGROUND OF THE INVENTION

Methods and apparatus for 3D scanning of the human body form are known. Systems embodying such methods and apparatus are commercially-available from Real 3D, Inc. of Orlando, Fla., Textile/Clothing Technology Corporation of Cary, N.C., and Cyberwave Laboratory Inc. of Monterrey, Calif.

Such systems generally employ a beam of light that is reflected off a human subject and measured by a detector which receives the reflected beam. The point of contact between the reflected beam and the human subject is then determined in three dimensions. However, these systems generally require the human subject being scanned remove his/her clothing prior to scanning a wear a special tight-fitting garment having proper reflection properties with respect to the employed wavelength in order to ensure that the points of contact are of the human body form, and not of external garments, thus providing a more accurate scan.

By way of explanation, a beam of energy, such as light, impacting a surface of a given material generally interacts with the material in any of three ways: reflection, transmission, and absorption. A reflected beam is reflected from the surface at an angle of reflection equal to the impact angle in the case of specular reflection or a multitude of angles for the case of disperse reflection. A transmitted beam is transmitted through the material and emerges from the back surface of the material. The energy of an absorbed beam is at least partially absorbed by the material. A beam may be partially reflected, partially transmitted, and partially absorbed by the material such that the energy of the reflected beam, the amount of energy absorbed by the material, and the energy of the beam emerging from the back side of the material added together equals the initial impact energy of the source beam.

The ratio between the transmission (T) and reflection (R) properties of a material with respect to a given beam wavelength depend in part on such parameters as angle of impact, beam cross-section, and collimation. While the T/R ratio varies between 0 to $\infty$, it will typically have a measurable finite value. Current scanning techniques implicitly assume working conditions of either R>>T for scanning an exposed surface or, for "see-through" scanning of a surface through an outer layer of material R>>T for the inner surface and T>>R for the outer layer of material, or effectively transparent to the radiation employed. However, human skin and a large variety of materials found in clothing exhibit an R≈T behavior for a variety of wavelengths. Experimentation has shown that where an inner or target surface (I), such as skin, is scanned through an outer layer of material (O), such as clothing, the ratio $\epsilon$ of the intensity of the beam reflected by the inner surface ($I_{RB}$) to that of the beam reflected by the outer layer ($O_{RB}$) may be expressed as $I_{RB}=\epsilon \cdot O_{RB}$ with $0.01<\epsilon<0.5$. Such a ratio does not comply with the assumptions of surface scanning or "see-through" scanning described above. Thus, current scanning techniques do not exist that allow the human body form to be scanned while the human subject is wearing normal clothing as they work under an implicit assumption of $\epsilon<<1$, compatible with surface scanning assumptions only.

The disclosures of all patents, patent applications, and other publications mentioned in this specification and of the patents, patent applications, and other publications cited therein are hereby incorporated by reference.

SUMMARY OF THE INVENTION

The present invention seeks to provide improved methods and apparatus for 3D scanning of the human body form that allows for a subject to be scanned while wearing normal, loose-fitting clothing. Two reflections are generated for each scanned point, an inner surface reflection $I_{RB}$ from the subject's skin and an outer layer reflection $O_{RB}$ from the subject's clothing, exploiting the difference in the T/R characteristics of clothing and human skin under suitable conditions. In order to distinguish between the skin-reflected beam $I_{RB}$ and the clothes-reflected beam $O_{RB}$ in the equation $I_{RB}=\epsilon \cdot O_{RB}$ the value of $\epsilon$ is optimized for various clothing types, and signal processing techniques are used to extract $I_{RB}$ from the combined reflected beam signals. The T/R characteristic differences vary with the type of clothing and may be global (uniform) or local, with a particular fabric exhibiting a random or quasi-random local variation in its ability to transmit radiation due to differences in color, pattern, or texture.

There is thus provided in accordance with a preferred embodiment of the present invention a method for scanning an inner surface through an outer layer of material, the method including the steps of a) creating an energy beam with a wavelength, intensity, cross-section, and impact angle that, when impacted onto the outer layer of material, is sufficient to be at least partly reflected by the outer layer of material, thereby forming an outer-layer reflected beam, to be at least partly transmitted in a first direction through the outer layer of material and onto the inner surface, to be at least partly reflected by the inner surface, thereby forming an inner-surface reflected beam, and to be at least partly transmitted in a second direction through the outer layer of material, b) impacting the energy beam onto the outer layer of material, c) detecting the outer-layer reflected beam and inner-surface reflected beam, d) distinguishing between the outer-layer reflected beam and inner-surface reflected beam, and e) determining from the inner-surface reflected beam a point of incidence between the energy beam and the inner surface in three dimensions.

Further in accordance with a preferred embodiment of the present invention the method further includes performing steps a)–e) a plurality of times, thereby yielding a plurality of the points of incidence.

Still further in accordance with a preferred embodiment of the present invention steps a)–e) are performed upon a clothed human body.

Additionally in accordance with a preferred embodiment of the present invention the wavelength is between 400 to 2000 nm, the cross-section is between 0.005 to 3 cm, the intensity is between 0.02 to 100 mW, and the impact angle is between 0° to 85°.

Moreover in accordance with a preferred embodiment of the present invention the distinguishing step includes distinguishing using either of time-domain analysis and spatial-domain analysis.

Further in accordance with a preferred embodiment of the present invention the energy beam has a repetition rate between 11 Hz to 80 MHz.

There is also provided in accordance with a preferred embodiment of the present invention apparatus for scanning an inner surface through an outer layer of material including an energy beam source operative to a) create an energy beam with a wavelength, intensity, cross-section, and impact angle that, when impacted onto the outer layer of material, is sufficient to be at least partly reflected by the outer layer of material, thereby forming an outer-layer reflected beam, to be at least partly transmitted in a first direction through the outer layer of material and onto the inner surface, to be at least partly reflected by the inner surface, thereby forming an inner-surface reflected beam, and to be at least partly transmitted in a second direction through the outer layer of material and b) impact the energy beam onto the outer layer of material, a detection unit operative to detect the outer-layer reflected beam and inner surface reflected beam, and a processing unit operative to distinguish between the outer-layer reflected beam and inner-surface reflected beam and determine from the inner-surface reflected beam a point of impact between the energy beam and the inner surface in three dimensions.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
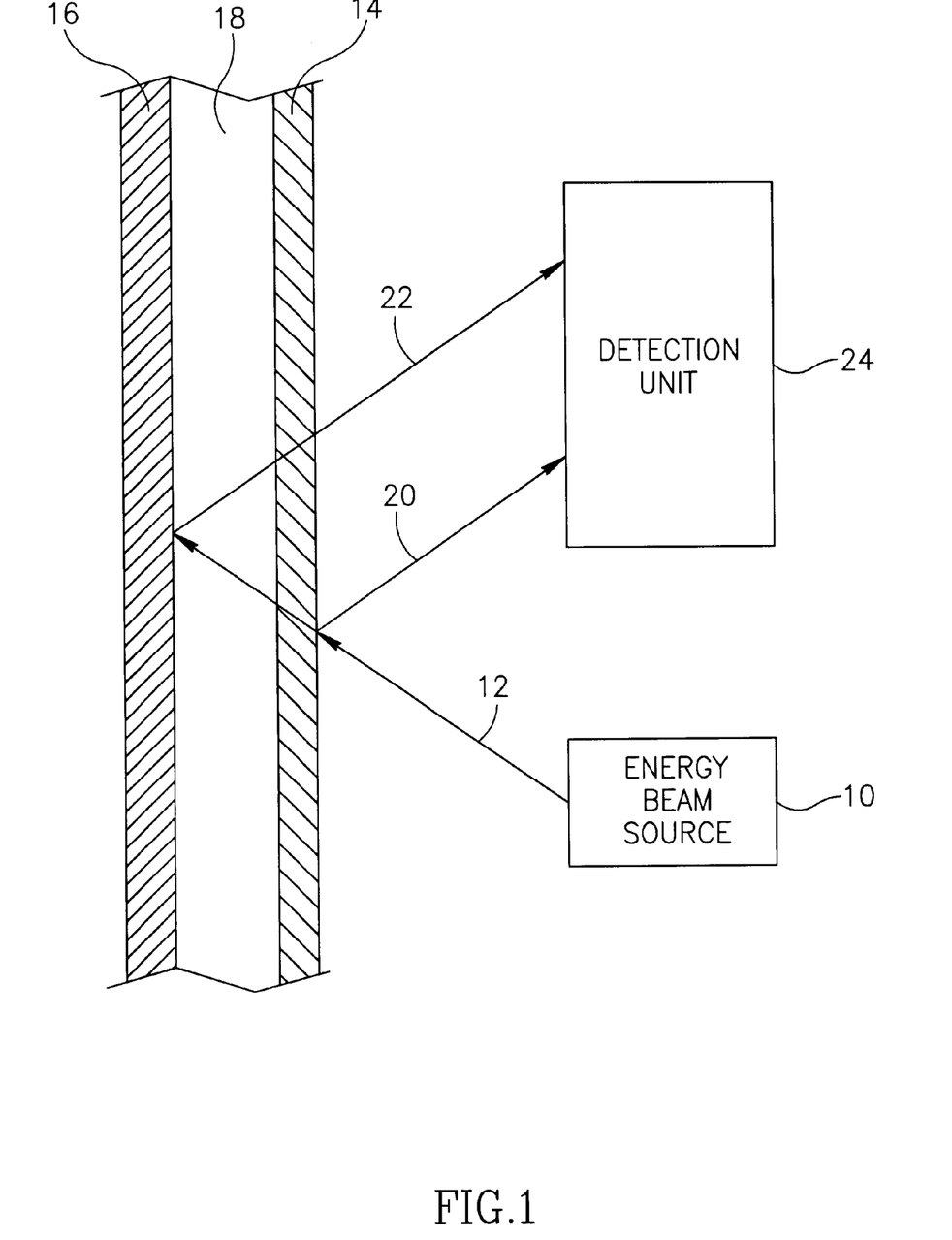
FIG. 1 which is a simplified graphical illustration of human body form scanning apparatus constructed and operative in accordance with a preferred embodiment of the invention.

Reference is now made to FIG. 1 which is a simplified graphical illustration of human body form scanning apparatus constructed and operative in accordance with a preferred embodiment of the invention. An energy beam source 10 is provided for projecting an energy beam 12 onto an outer layer 14, such as of clothing, and an inner surface 16, such as human skin. Typically, the reflectance and transmittance properties of any given material depend on its surface characteristics, material and chemical composition, and refractive index, as well as the wavelength of impact energy beam, beam cross-section, and angle of impact. Given the known transmittance and reflectance of outer layer 14, inner surface 16, and any intermediate layers 18, such as air, energy beam 12 is preferably of a sufficient wavelength, cross-section, angle of impact, and intensity such that it is partly reflected by outer layer 14, as shown by an outer layer reflection beam 20, transmitted through outer layer 14, reflected by inner surface 16, and transmitted through outer layer 14, as shown by an inner surface reflection beam 22. A detection unit 24 typically receives both the outer layer reflection beam 20 and the inner surface reflection beam 22 for signal processing as is described in greater detail hereinbelow.

Energy beam source 10 preferably has a wavelength of 400 to 2000 nm, a beam cross-section of 0.005 to 3 cm, an intensity of 0.02 to 100 mW, and an impact angle of 0° to 85°. Energy beam source 10 may also be implemented in a variety of ways in order to produce an energy beam that produces the desired outer layer and inner surface reflections. For example, a continuous source beam may be used where the beam amplitude is constant for each basic measurement cycle (BMC) which is defined herein as the time interval required to scan a single point on inner surface 16. Alternatively, a pulsed source beam may be used where the amplitude varies within a BMS. A single energy beam source 10 may be used to scan each point sequentially in a vector mode, or, alternatively, an array of energy beam sources may be used to scan multiple points simultaneously in a raster mode. The energy beam characteristics, including intensity, wavelength, cross-section, and impact angle may be optimized to best conform with assumed uniform T/R characteristics of outer layer 14 and inner surface 16 over an extended area, typically 10 cm². Alternatively, a "statistical mode" may be employed where the energy beam characteristics are optimized to best conform with a spatial variation of the T/R characteristics of at least one of the two layers. The statistical nature of the T/R variability is best taken advantage of by optimizing the beam cross section, typically by employing beams having a cross-section of less than 200 microns.

Energy beam 12 may be a single monochromatic beam, a wideband beam comprising radiation of a multiplicity of wavelengths, or a sequence of beams of various frequencies. Where a wideband beam is employed the reflected radiation, comprising at least part of the initial multiplicity of wavelengths, is simultaneously intercepted in either wavelength-sensitive mode or a wavelength-insensitive mode. The wavelength-sensitive mode may be implemented by using a plurality of detectors, each sensitive to a single wavelength, in conjunction with a demultiplexer which decomposes the intercepted wideband beam into multiple single-wavelength beams and directs the beams to the appropriate detectors. Alternatively, the detection may be performed by using a single detector and individually encoded radiation components. Such encoding maybe achieved either through polarization or any suitable time-domain based encoding method known in the art. The wavelength-insensitive mode may be implemented by employing a single detector having a broadband sensitivity for intercepting the totality of the reflected energy. Where a sequence of beams is employed multiple beams are targeted at each point and detected individually. Each individual beam may be continuous or pulsed and may have similar or different intensity levels and/or cross-sections. The sequencing may be source-based, where a number of individual beam sources are switched sequentially and detected by a single detector. Alternatively, the sequencing may be detector-based, where a number of individual beam sources operate in parallel and where a single detector with broad sensitivity is used in conjunction with a series of filters which are switched sequentially.

Figure 2:
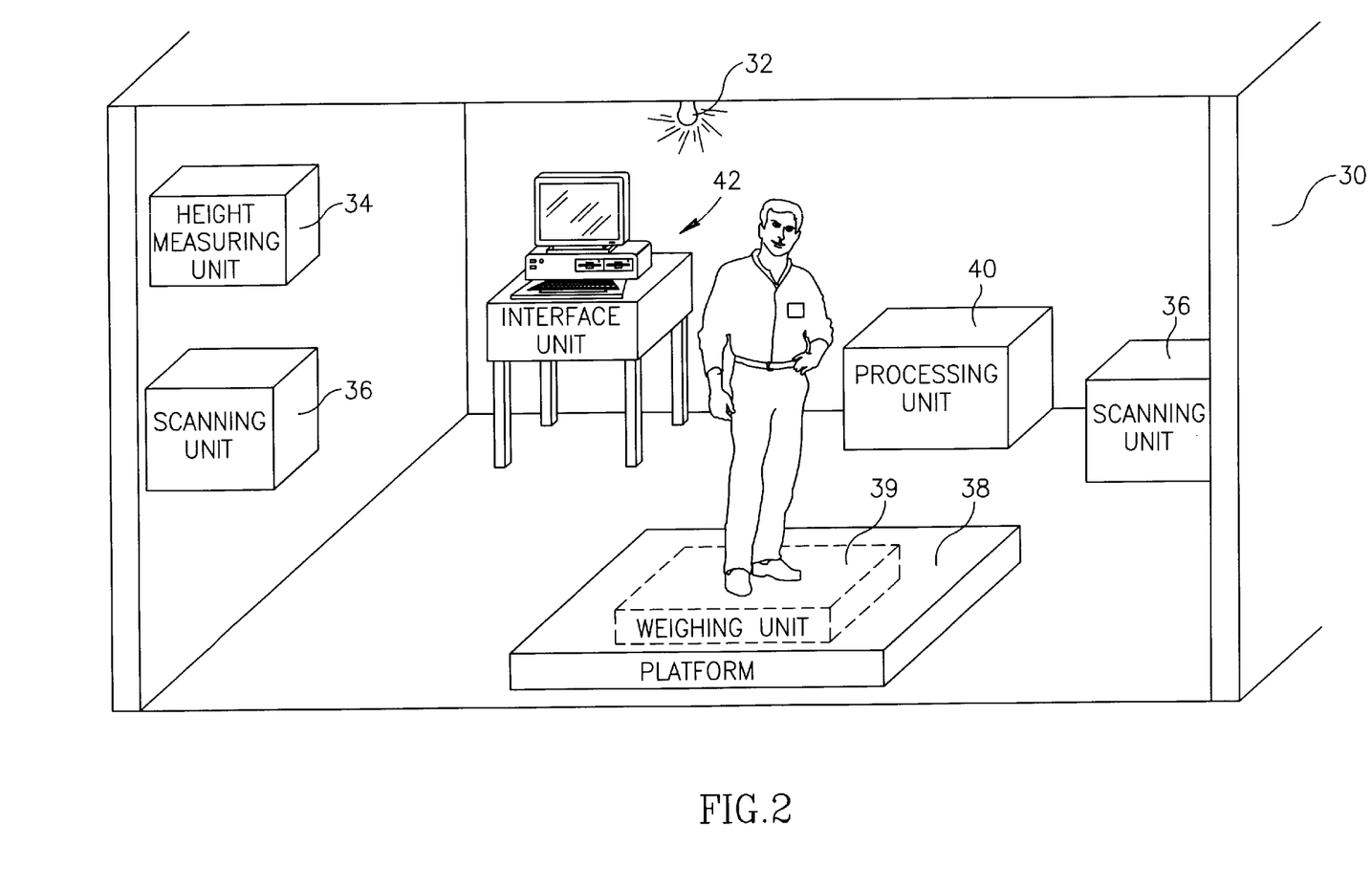
FIG. 2 which is a simplified pictorial illustration of a scanning system constructed and operative in accordance with a preferred embodiment of the present invention.
Figure 3:
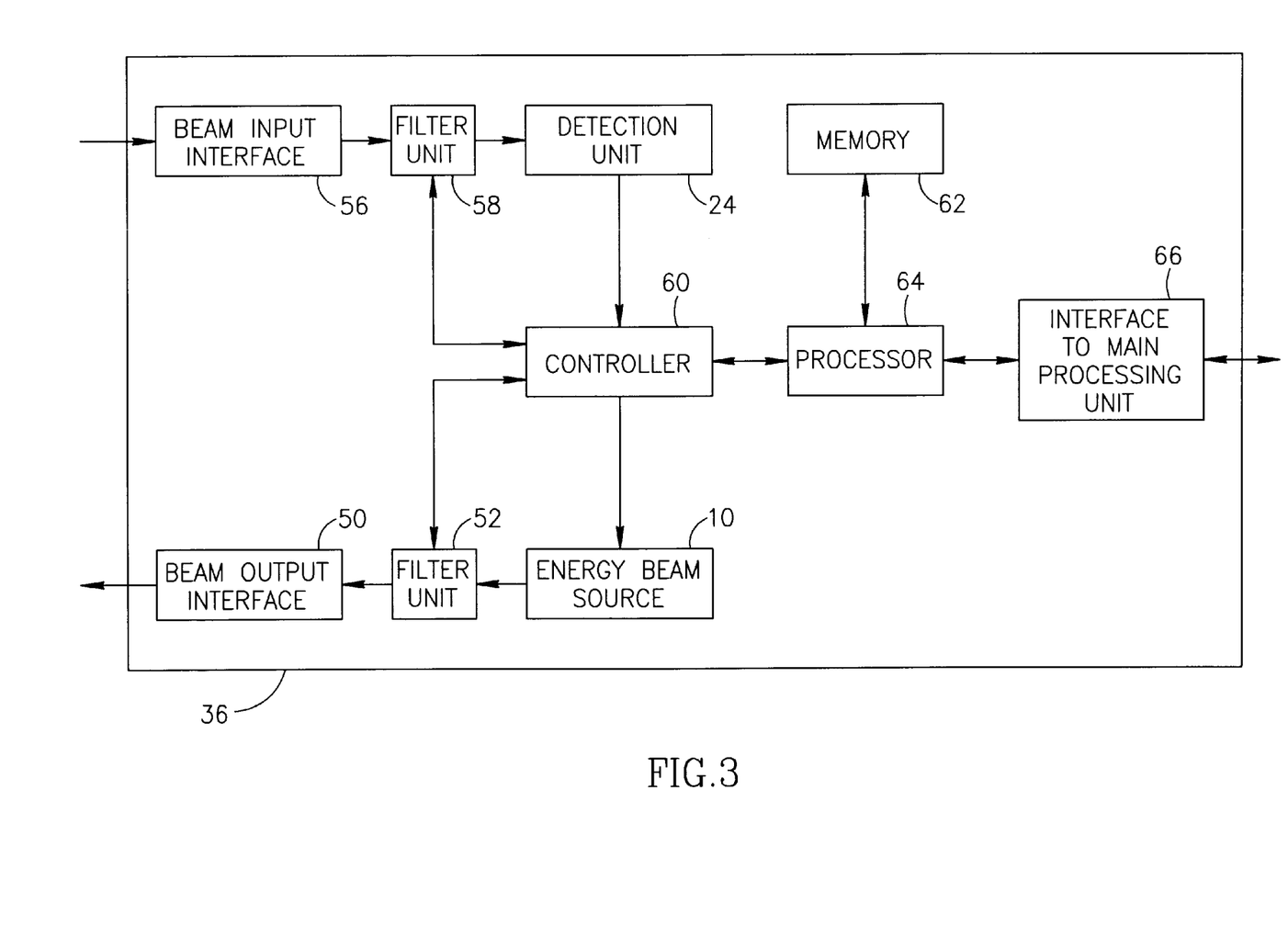
FIG. 3 which is a simplified block diagram of scanning unit 36 of FIG. 2, constructed and operative in accordance with a preferred embodiment of the present invention.

Reference is now made to FIG. 2 which is a simplified pictorial illustration of a scanning system constructed and operative in accordance with a preferred embodiment of the present invention. A scanning booth 30 is preferably provided, including a lighting unit 32 that may be any controllable, suitable filtered light source for general purpose illumination of the booth. A height measuring unit 34 is also typically provided and may be any suitable non-contact height measuring unit known in the art, such as a range finder. One or more scanning units 36, described in greater detail hereinbelow with reference to FIG. 3, are also typically provided that operate in accordance with the principles described hereinabove with reference to FIG. 1. Height measuring unit 34 preferably determines the height of the person being scanned prior to scan initiation in order to calibrate the scanning range of scanning units 36. A platform 38 is also typically provided together with a weighing unit 39, which may be any suitable load cell or weighing apparatus known in the art. Weighing unit 39 preferably determines the weight of the person being scanned prior to scan initiation which may be used to determine the accuracy of a scanned form by comparing its volume to an estimated volume for the scanned person based on his/her height and weight. A main processing unit 40 is also provided for controlling any of the elements of booth 30, and typically comprises any known computer means known in the art, including network communications means or other communications means for transmitting scanning data. Main processing unit 41 may also be used to analyze the scanning data in accordance with the methods described hereinbelow with reference to FIGS. 5, 6, and 7. An interface unit 42, described in greater detail hereinbelow with particular reference to FIG. 4 is also typically provided.

Reference is now made to FIG. 3 which is a simplified block diagram of scanning unit 36 of FIG. 2, constructed and operative in accordance with a preferred embodiment of the present invention. Scanning unit 36 includes energy beam source 10 and detection unit 24, described hereinabove with reference to FIG. 1. Energy beam source 10 is preferably provided with a beam output interface 50, including an appropriate lens system, as well as a filter unit 52. Energy beam source 10 may comprise a broadband source such as a quartz-tungsten-halogen (QTH) lamp or several monochromatic laser diode (LD) sources which may be combined to generate a wideband beam by using an appropriate LD power combiner or multiplexer such as the WDM series, commercially available from Oz Optics of Carp, Ontario, Canada. The multiplicity of LD sources may also be sequentially modulated. Detection unit 24 is also typically provided together with a beam input interface 56, including an appropriate lens system, as well as filter unit 58. Detection unit 24 may be a CCD array, a suitable position sensing detector (PSD) or PSD array, a photomultiplier (PMT), or an avalanche photodiode. Filter units 52 and 58 may include polarization filters having a constant polarization, polarization rotators/analyzers such as the FPR series from Oz Optics or equivalents, low or high filters, or narrow or broad-band window filters as known in the art or any suitable combinations thereof. A controller 60, memory 62, processor 64, and main processing interface 66 are also preferably provided for controlling elements of scanning unit 36 and for communicating with main processing unit 40 (FIG. 2).

Figure 4:
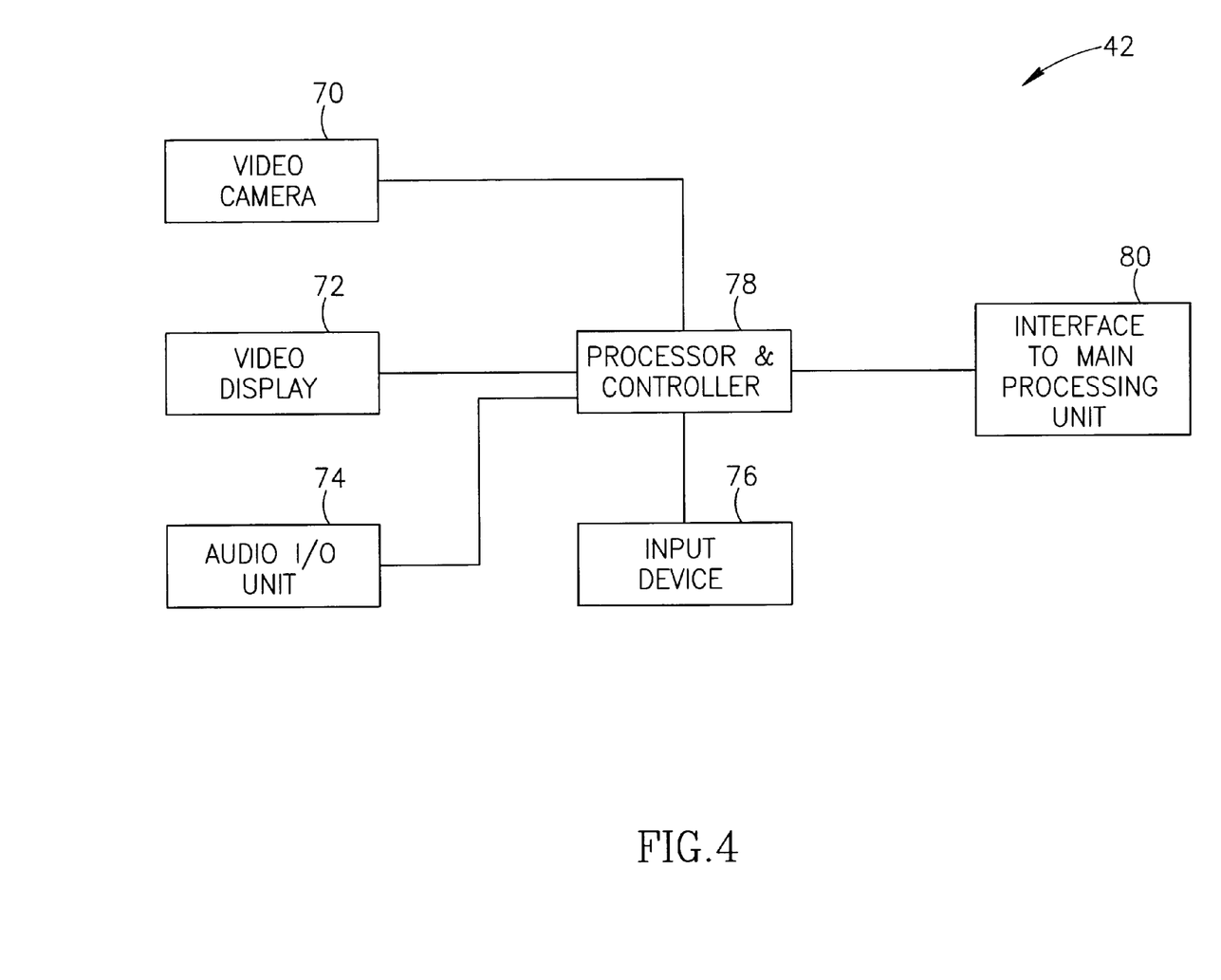
FIG. 4 which is simplified block diagram of interface unit 42 of FIG. 2, constructed and operative in accordance with a preferred embodiment of the present invention.

Reference is now made to FIG. 4 which is a simplified block diagram of interface unit 42 of FIG. 2, constructed and operative in accordance with a preferred embodiment of the present invention. Interface unit 42 preferably includes one or more video cameras 70 for taking a 3D video image of a subject's head which will later be used to generate a full-color scaled image of the scanned person. At least one of the video cameras is typically used prior to scanning in order to determine the scanned subject's posture. For this purpose, a full-body image of the individual is analyzed against a set of constant reference points relative to the coordinate system of the booth interior. The image may then be compared with a preprogrammed set of silhouettes to interactively guide the subject to assume an optimal scanning posture. A video display 72 is used to display visual information including a representation of the desired scanning posture. An audio I/O unit 74 including a speaker, a microphone, and a voice recognition module is also provided. An additional input device 76 may additionally be provided for input of the scanned subject's personal information and may comprise any input means known in the art other than voice. A processor/controller 78 and main processor interface 80 are also preferably provided for controlling elements of interface unit 42 and for communicating with main processing unit 40 (FIG. 2).

Figure 5:
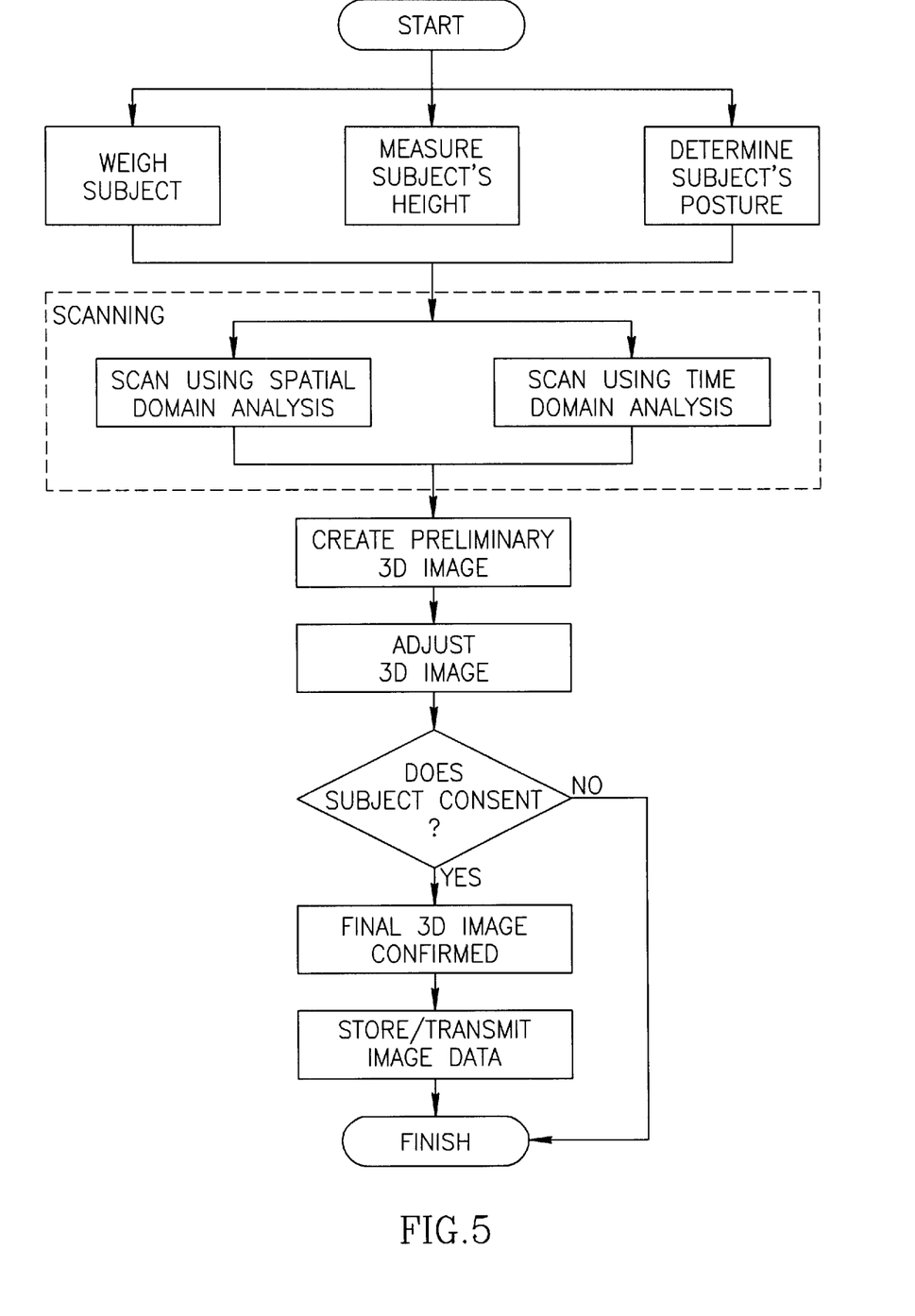
FIG. 5 which is a simplified flowchart illustration of a method of operation of the scanning system of FIG. 2, operative in accordance with a preferred embodiment of the present invention.

Reference is now made to FIG. 5 which is a simplified flowchart illustration of a method of operation of the scanning system of FIG. 2, operative in accordance with a preferred embodiment of the present invention. Typical operation begins when a clothed subject enters booth 30. The quality of the scanned data is dependent in part upon the scanned subject's posture as viewed from the scanning units 36. Therefore, the subject is preferably assisted by interface unit to assume an optimal posture. The system analyzes the subject's video image, recognizes the subject's main features, such as the subject's head, hands, legs, etc., using known pattern recognition techniques, and instructs the subject using audiovisual cues to assume a predefined and optimal posture. Preferably, the subject is weighed and measured for height. The height measurement is used by the system to optimize the scanned area, and the accuracy of the subject's scanned form is determined by comparing its volume to an estimated volume for the scanned subject based on his/her height and weight.

Scanning begins once the system determines that the subject is in an optimal posture. Energy beam 12 is then preferably impacted onto the clothed subject at multiple points along the subject's form and to the extent of the subject's height. During scanning points of incidence between the energy beam 12 (FIG. 1) and the subject's skin (i.e., inner surface 16) are determined in three dimensions using spatial domain analysis, time domain analysis, or both for comparison, in accordance with techniques well known in the art and as it is described in greater detail hereinbelow with reference to FIGS. 6 and 7. Scanning typically continues until all points on the subject's form have been impacted with energy beam 12 and/or a predefined maximum scanning time has elapsed. Upon completion of the scanning process the system analyzes the collected data and preferably creates a preliminary 3D digital image of the subject based on the identified points of incidence. The system may also determine a quality factor for the image, determining, for example, the percentage of the subject's body form area for which no points of incidence were determined in relation to the subject's entire body area. Based upon this quality factor the system may either generate a final digital image or transmit the raw data to a workstation operated by a trained and skilled operator for image adjustment where scan gaps are adjusted using CAD tools in accordance with a set of predefined rules. The workstation may be located in the vicinity of the booth or located off-site. Upon completion of the local digital image generation the subject is preferably asked to grant consent to the final submission and storage of his personal digital image. If consent is granted the system may provide the subject with a confirmation and transmits the image data to a central server for storage.

Figure 6:
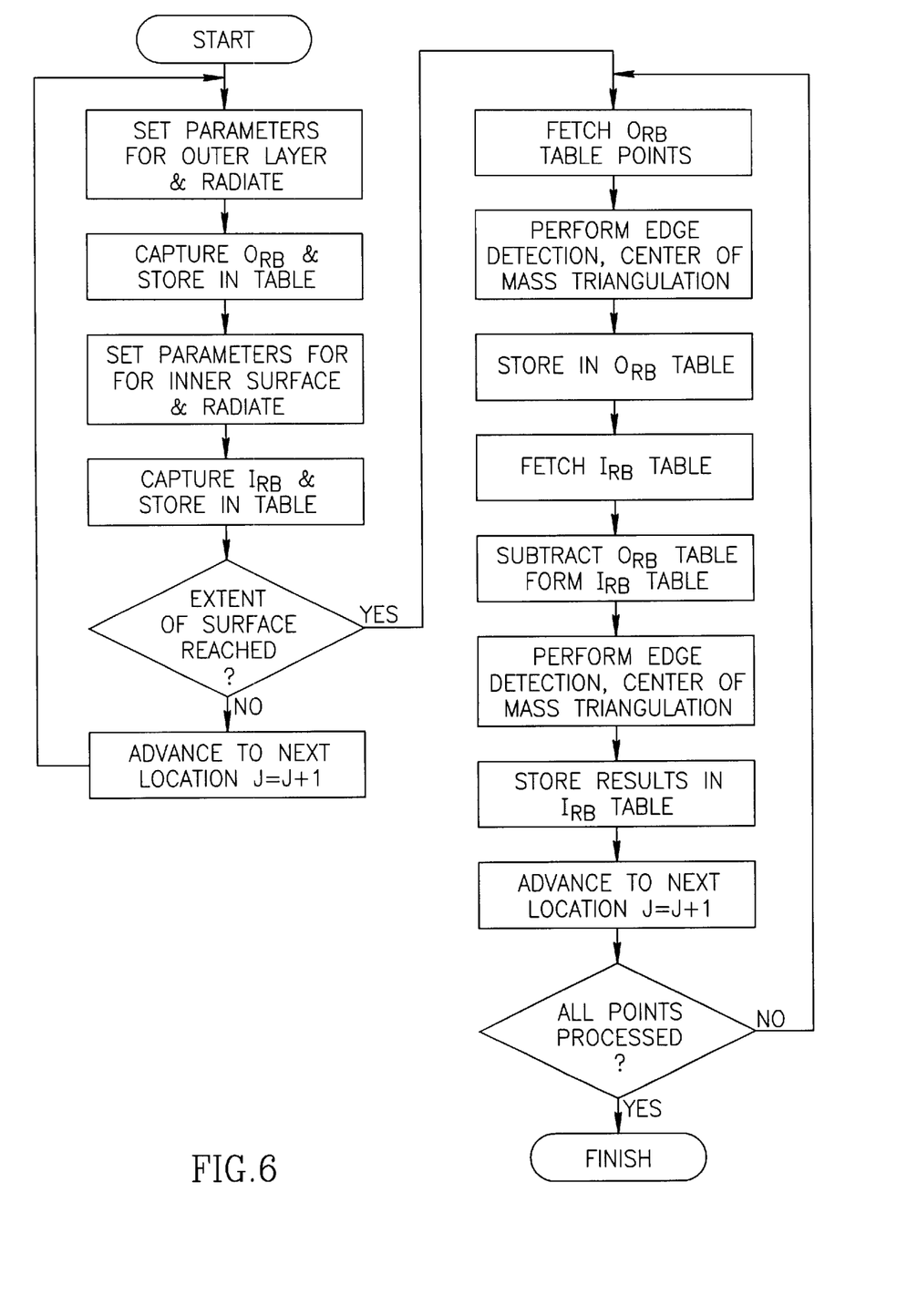
FIG. 6 is a simplified flowchart illustration of a method of scanning using spatial domain analysis, operative in accordance with a preferred embodiment of the present invention.

Reference is now made to FIG. 6 which is a simplified flowchart illustration of a method of scanning using spatial domain analysis, operative in accordance with a preferred embodiment of the present invention. In the method shown two coordinates maps are generated, one for the inner surface and another for the outer layer. Each said coordinate map comprises the spatial X, Y, and Z coordinates for the resolved scanned points. Using these coordinates the system may reconstruct a 3D digital image of the scanned target, including a 3D image of the inner surface as well as of the outer layer. The spatial domain analysis process comprises two sub-processes: 1) the collection and storage of the data of the actual scan and 2) the analysis of the data and the generation of coordinate maps of the scanned points. The collection and storage are performed during the actual scan, while the analysis may be performed in real-time or off-line.

An initial set of parameters for the scanning of a given subject is typically determined by taking a few single-point measurements during the initial posture determination process (FIG. 5). For example, the beam intensity level, cross-section, wavelength, polarization, and incident angle are typically calibrated to achieve optimal reflection and dispersion characteristics by means of such single-point measurements.

During the data collection phase each point is scanned using two differential parameter sets, the first optimized for the inner surface and the second for the outer layer. Typically, the beam parameters are first optimized for scanning of the outer layer. The beam intensity and cross-section are preferably adjusted such as to result in a single reflection. This may be performed using closed loop feedback control techniques or any other suitable technique known in the art. Typically, the optimization procedure begins with a beam having a predefined cross-section and low-level intensity. Both parameters are then varied until the optimal reflection is achieved. The outer layer reflected beams ($O_{RB}$) are received by the detector, such as a charge-coupled device (CCD). Typically, the $O_{RB}$ is detected using an appropriate variable polarization filter and stored in an outer-layer image table as a series of spot images having a size and intensity distribution dependent on the degree of polarization. Alternatively, the $O_{RB}$ is detected without a polarization filter. Next, the beam parameters are optimized for scanning of the inner surface in a manner similar to that which was described above for the outer layer, until a second reflection results for each incidence point. The reflected beam data are likewise stored in an inner-surface image table. Processing continues until the subject is completely scanned within the predetermined height parameters.

During the data analysis phase the raw image data are preferably fetched from the inner-surface and outer layer image tables into memory. Both sets of data are used to generate the X, Y, and Z coordinates of the scanned points to form a coordinate map of both the inner surface and the outer layer. The calculation of the spatial coordinates may be performed using conventional tools and techniques such as the Image Processing Library V2.2, commercially-available from EPIX Inc. of Buffalo Grove, Ill., USA, as described in detail hereinbelow. A digital spot image of reflected radiation spots is typically generated for both the outer layer and the inner surface by means of edge detection functions such as "Kirsch—pxip8_3×3kirsch" or "Sobel—pxip8_3× 3sobel." Following the detection stage the center of mass region of the spot image may be calculated by means of the "pxirp8_masscenter" function. The spatial coordinates of the spot are then calculated by way of triangulation based on the known geometry of the source, the detector, and the optical system using conventional techniques. The X, Y, and Z coordinates corresponding to the point representing the outer layer and calculated from the scan data are then stored in corresponding fields in the outer-layer image table.

The spatial coordinates of the inner surface are calculated in a similar manner using the spot image data by removing the $O_{RB}$ image from the raw data stored in the inner-surface image table by means of an image pair pixel subtraction function, "pxip8_pairsub." Both images are preferably normalized prior to the subtraction operation. The X, Y, and Z coordinates corresponding to the points representing the inner surface are then stored in corresponding fields in the inner-surface image table. The process described above for the inner surface and the outer layer is then repeated for all spot images corresponding to the scanned points stored in both tables.

Figure 7:
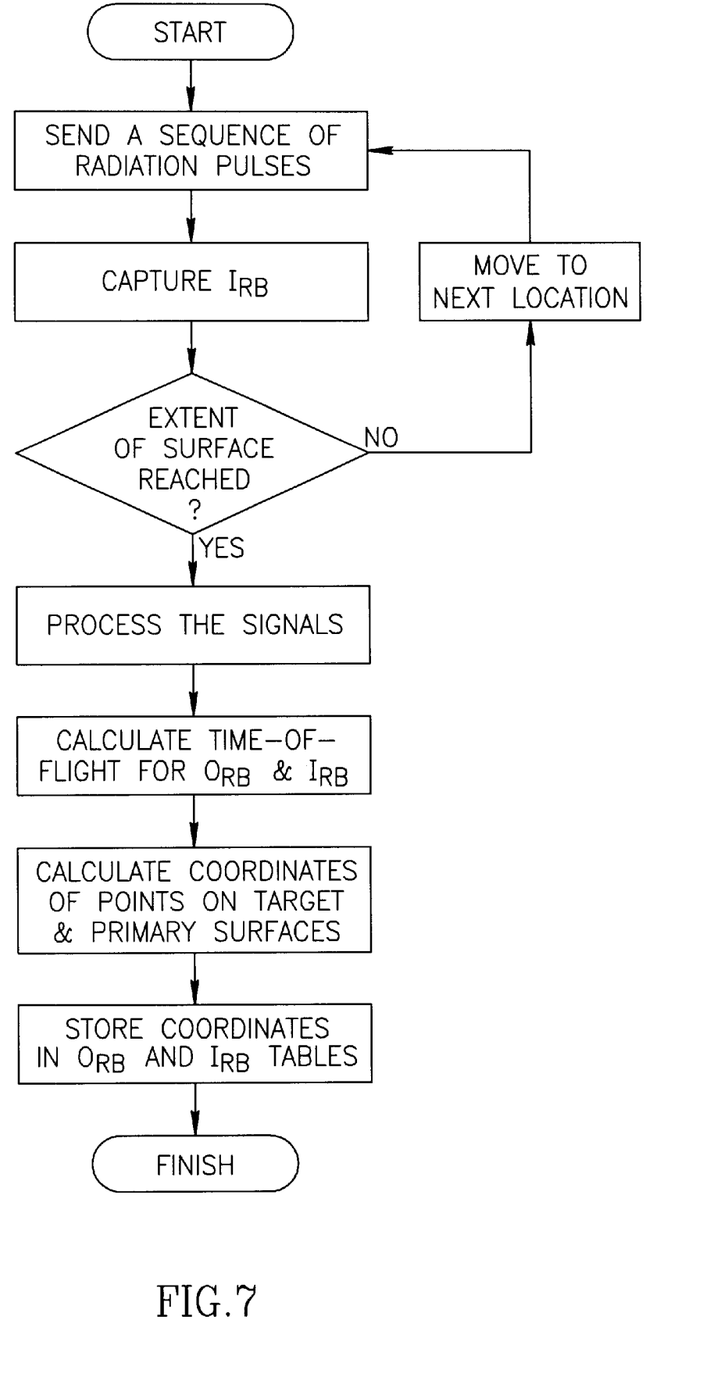
FIG. 7 which is a simplified flowchart illustration of a method of scanning using time domain analysis, operative in accordance with a preferred embodiment of the present invention.

Reference is now made to FIG. 7 which is a simplified flowchart illustration of a method of scanning using time domain analysis, operative in accordance with a preferred embodiment of the present invention. In the method shown radiation beam 12 comprises a sequence of pulses that impact outer layer 14 and subsequently inner surface 16, whereupon the pulses are reflected off of outer layer 14 and inner surface 16. The pulses are preferably sub-nanosecond pulses with a repetition rate of 1 Hz to 80 MHz, such as is provided by a PDL 800, commercially-available from PicoQuant of Berlin, Germany. The reflected beams are then detected and stored using a detector such as an avalanche photodiode or a R632/01 PMT, commercially-available from Hamamatsu of Hamamatsu City, Japan. Scanning preferably continues for each subsequent surface location until the entire target surface is scanned. The detected and stored signals may be processed using a device such as SPC 530 from PicoQuant having a time resolution of 7 picoseconds corresponding with a spatial resolution of approximately 2 mm. The stored raw data is preferably fetched from the memory of the SPC530 device, and the time-of-flight corresponding to each reflected beam of both the inner surface and the outer layer may then be calculated using conventional techniques, such as those employed by the SPC530 device. The corresponding vector length originating from the detector to each point of incidence between the energy beam 12 and the inner surface 16 or the outer layer 14 may then be calculated from the time-of-flight data using the formula $$V_{Length}=c*(ToF/2)$$

where c=speed of light and Tof=Time of Flight. The spatial X, Y, and Z coordinates of the scanned points are then calculated from the vector length and scan geometry of the source and the detector and stored in corresponding fields in the inner-surface image table and the outer-layer image table respectively.

The following Tables A and B represent an exemplary set of operating parameters used to generate inner-surface reflected beams ($I_{RB}$) and outer-layer reflected beams ($O_{RB}$) where spatial domain analysis is used to resolve the points of incidence:

TABLE A

| | |
|---|---|
| Human Skin: | Caucasian |
| Detector: | B&W CCD camera such as SSCM257CE from Sony (with infrared filter removed) equipped with an f-stop 1.2 VCLS12XEA lens. |
| Radiation sources: | HL6720G 670 nm, 5 mW Hitachi Laser Diode (LD), CW |
| | LT027MD 780 nm, 10 mW Sharp LD, CW |
| | HL8325G 830 nm, 40 mW (LD), CW |
| Beam characteristic: | Collimated 5 mm |
| | Collimated 8 mm |
| | Collimated 0.3 mm |
| Beam intensity: | 4.5–5 mW, 670 nm, 5 & 8 mm beam diameter |
| | 8–10 mW, 780 nm, 5 & 8 mm beam diameter |
| | 5 mW and 30 mW, 830 nm, |
| | 5 & 8 mm beam diameter |
| | 0.018 mW, 670 & 830 nm, 0.3 mm beam diameter |
| | 0.126 mW, 830 nm, 0.3 mm beam diameter |

The beam intensity was measured with a S2OMM/M silicon power meter from Thorlabs, Inc. of Newton, NJ.

TABLE B

| Fabric | Impact angle (θ) [deg] | Gap (fabric to skin surface) [mm] | Wavelength [nm] | Intensity/diameter [mW]/[mm] |
|---|---|---|---|---|
| typical summer fabric, linen, natural color | 0 | 5 to 15 mm | 670 | 4.5/5, 4.5/8, 0.018/0.3 |
| | 20 | | 780 | 4.5/5 |
| | 45 | | 830 | 4.5/5, 4.5/8, 0.126/0.3 |
| typical wool fabric (formal dress), dark color | 0 | 5 to 15 mm | 670 | 4.5/5, 0.018/0.3 |
| | 20 | | 780 | — |
| | 45 | | 830 | 5/5 |
| typical knitwear (tricot), cotton, black | 0 | 5 to 15 mm | 670 | 4.5/5, 0.018/0.3 |
| | 20 | | 780 | — |
| | 45 | | 830 | 5/5, 0.126/0.3 |

While the methods and apparatus disclosed herein may or may not have been described with reference to specific hardware or software, the methods and apparatus have been described in a manner sufficient to enable persons of ordinary skill in the art to readily adapt commercially available hardware and software as may be needed to reduce any of the embodiments of the present invention to practice without undue experimentation and using conventional techniques.

While the present invention has been described with reference to a few specific embodiments, the description is intended to be illustrative of the invention as a whole and is not to be construed as limiting the invention to the embodiments shown. It is appreciated that various modifications may occur to those skilled in the art that, while not specifically shown herein, are nevertheless within the true spirit and scope of the invention.

What is claimed is:

1. Apparatus for scanning an inner surface through an outer layer of material comprising:
    an energy beam source operative to create an energy beam with a wavelength; intensity, cross-section, and impact angle that when impacted onto said outer layer of material is sufficient to be at least partly reflected by said outer layer of material and at least partly transmitted in a first direction through said outer layer of material and onto said inner surface, to be at least partly reflected by said inner surface, and to be at least partly transmitted in a second direction through said outer layer of material;
    a detection unit operative to detect an outer-layer reflected beam and an inner-surface reflected beam; and
    a processing unit operative to distinguish between said outer-layer reflected beam and said inner-surface reflected beam and to determine from said inner-surface reflected beam a point of impact between said energy beam and said inner surface in three dimensions.

2. Apparatus according to claim 1 wherein said energy beam source is operative to impact said energy beam upon said inner surface at a plurality of points.

3. Apparatus according to claim 1 wherein said energy beam source is operative to impact said energy beam upon a cloned human body.

4. Apparatus according to claim 1 wherein said wavelength is between 400 to 2000 nm, said cross-section is between 0.005 to 3 cm, said intensity is between 0.02 to 100 mW, and said impact angle is between 0° to 85°.

5. Apparatus according to claim 1 wherein said processing unit is operative to distinguish using either of time-domain analysis and spatial-domain analysis.

6. Apparatus according to claim 1 wherein said energy beam has a repetition rate between 1 Hz to 80 MHz.

7. A method of scanning an inner surface through an outer layer of material comprising the steps of:
    creating an energy beam with a wavelength, intensity, cross-section, and impact angle that when impacted onto said outer layer of material is sufficient to be at least partly reflected by said outer layer of material and at least partly transmitted in a first direction through said outer layer of material and onto said inner surface, to be at least partly reflected by said inner surface, and to be at least partly transmitted in a second direction through said outer layer of material;
    impacting said energy beam onto said outer layer of material;
    detecting an outer-layer reflected beam and an inner-surface reflected beam;
    distinguishing between said outer-layer reflected beam and inner-surface reflected beam; and
    determining from said inner-surface reflected beam a point of incidence between said energy beam and said inner surface in three dimensions.

8. A method according to claim 7 and further comprising performing said steps a plurality of times.

9. A method according to claim 7 wherein said steps are performed upon a clothed human body.

10. A method according to claim 7 wherein said wavelength is between 400 to 2000 nm, said cross-section is between 0.005 to 3 cm, said intensity is between 0.02 to 100 mW, and said impact angle is between 0° C. to 85°.

11. A method according to claim 7 wherein said distinguishing step comprises distinguishing using either of time-domain analysis and spatial-domain analysis.

12. A method according to claim 7 wherein said energy beam has a repetition rate between 1 Hz to 80 MHz.

* * * * *